United States Patent [19]
Bearer

[11] Patent Number: 5,952,235
[45] Date of Patent: Sep. 14, 1999

[54] DETECTION OF TERATOGEN EXPOSURE

[75] Inventor: Cynthia Bearer, Pulaski, Pa.

[73] Assignee: Case Western Reserve University, Ohio

[21] Appl. No.: 08/837,156

[22] Filed: Apr. 14, 1997

[51] Int. Cl.$^6$ ..................................................... G01N 30/02
[52] U.S. Cl. ........................... 436/71; 436/127; 436/128; 436/132; 436/161
[58] Field of Search .............................. 436/71, 132, 127, 436/128, 161, 131, 173, 178; 210/656; 73/61.55, 61.52

[56] References Cited

U.S. PATENT DOCUMENTS 4,564,477  1/1986  Takigawa et al. .
5,094,960  3/1992  Bonomo .................................... 436/178

FOREIGN PATENT DOCUMENTS

WO 95/00631  1/1995  WIPO .............................. C12M 1/12

*Primary Examiner*—Jan Ludlow
*Attorney, Agent, or Firm*—Medlen & Carroll, LLP

[57] ABSTRACT

The present invention relates to methods for detecting teratogen exposure in neonates. In particular, the present invention is directed to the detection of prenatal (i.e., in utero) exposure to ethanol. In accordance with the present invention, fatty acid ethyl esters, produced as the by-products of non-oxidative ethanol metabolism are detected in samples such as meconium and cord blood.

26 Claims, 3 Drawing Sheets

| | | | |
|---|---|---|---|
| Data File Name | : C:\HPCHEM\1\DATA\52495\005F0101.D | | |
| Operator | : radmila | Page Number | : 1 |
| Instrument | : 5890 | Vial Number | : 6 |
| Sample Name | : 3-1200:1=6 Nida | Injection Number | : 1 |
| Run Time Bar Code: | | Sequence Line | : 1 |
| Acquired on | : 24 May 95  06:11 PM | Instrument Method | : FAEE6.MT |
| Report Created on | : 03 Aug 95 05:28 PM | Analysis Method | : FAEE6.MT |

DETECTION OF TERATOGEN EXPOSURE

FIELD OF THE INVENTION

The present invention relates to methods of detecting teratogen exposure and more particularly to detecting exposure to ethanol and other substances in the neonate.

BACKGROUND

Recent decades have seen a significant growth of basic, clinical, and epidemiologic investigation into the problem of teratogenesis due to environmental and external factors. With the realization that teratogens are an important cause of many serious and common abnormalities in neonates and children, has come an emphasis by health care agencies on preventing teratogenic exposure. Unfortunately, the goal of primary prevention through the avoidance of hazardous prenatal exposures remains substantially unrealized.

The striking proliferation of both therapeutic agents and chemical sources of pollution of our environment, coupled with self-medication and use of other chemical agents and non-therapeutic drugs by pregnant women makes drugs the most common cause of teratogenesis. Some reports suggest that the average pregnant women takes four or more medications, both prescribed and non-prescribed, during gestation. Among the drugs that are habitually used and abused, ethanol, tobacco and cocaine present the most significant public health problems.

There has been increasing concern about the effects of ethanol on the developing fetus. Ethanol is known to cross the placenta and cause deleterious effects on the developing fetus. Indeed, as little as 30 ml (1 ounce) of ethanol per day increases the risk of decreased birth weight; even moderate drinking may be responsible for an increased risk of spontaneous abortion (See, S. E. Hyman and N. H. Cassem, "13. III. Alcoholism," in D. C. Dale and D. D. Federman (eds.), *Medicine,* Scientific American, New York, page 11 [1995]); and Council on Scientific Affairs, J. Amer. Med. Assoc., 249:2517 [1983]).

Ethanol and Fetal Alcohol Syndrome

In the United States, as well as many other countries, ethanol leads the list of abused drugs. Epidemiologic studies suggest that prenatal damage from maternal ethanol abuse may be one of the most frequent recognizable causes of mental retardation, and is the most common preventable cause of birth defects in the United States (See e.g., C. F. Bearer et al., Pediatr. Res., 31:492–495 [1992]; T. W. Rall, "Hypnotics and Sedatives: Ethanol," in Gilman et al.,(eds), *Goodman and Gilman's The Pharmacological Basis of Therapeutics,* Pergamon Press, New York, page 373 [1990]).

Prenatal use of ethanol can result in a wide range of fetal abnormalities. The entire spectrum of prenatal alcohol damage, from mild to severe, is generally referred to as alcohol-related birth defects (ARBD). The frequency and severity of these anomalies appear to be dose-related and range from apparently clinically unaffected children to severely affected children suffering from fetal alcohol syndrome (FAS). Infants who have some, but not all of the physical characteristics of FAS are often referred to as exhibiting "Fetal Alcohol Effects" (FAE).

Although ethanol has been long suspected as being teratogenic, FAS has only been recently fully described (K. R. Warren and R. J. Bast, Public Hlth. Rept., 103:638–642 [1988]). FAS now surpasses Down syndrome and spina bifida as the leading cause of mental retardation in the world (E. L. Abel and R. J. Sokol, Drug Alcohol Depend., 19:51–70 [1987]), and the cost of caring for children afflicted with FAS is significant. Estimates put the annual cost of care in the United States at $74.6 million. Of this, about 78% involves expenses associated with mental retardation and low birth weight. The lifetime cost of treating one person with FAS has been estimated to be $1.4 million.

FAS is characterized by a distinctive facial appearance, prenatal onset growth deficiency, an increased frequency of developmental and mental retardation, and major congenital anomalies. Usually, FAS children suffer from central nervous system (CNS) deficiency (e.g., microcephaly and low IQ), slowness in growth, a characteristic group of facial abnormalities (e.g., short palpebral fissures, hypoplastic upper lip, and a short nose), and a variable array of major and minor malformations. Additional congenital abnormalities associated with FAS include cleft palate, cardiac malformations (especially atrial and ventricular septal defects), microphthalmia, hearing loss, joint anomalies, and a variety of dental and skeletal abnormalities. Neuropathologic examination often reveals significant abnormalities, neuronal migration occasionally associated with microcephaly, hydrocephaly, absence of the corpus callosum and cerebellar abnormalities. These infants commonly are short and of low birthweight. Often, they fail to thrive and do not grow as rapidly as other infants. In the newborn period, they are jittery or tremulous, a feature that is often confused with drug withdrawal symptoms. The pattern of wakefulness and sleep in affected newborns may also be disturbed. The neurologic abnormalities persist and in addition to developmental delay and mental retardation, such children are often poorly coordinated, tremulous and sometimes "hyperactive" in later life. In addition, children suffering from FAS have a greatly increased susceptibility to life-threatening, as well as minor infectious diseases, largely due to extensively impaired immune systems (See e.g., Johnson et al, Pediatr. Res., 15:908–911 [1981]). Although the exact mechanisms are not known, the effects of FAS may be due in part to the direct inhibition of embryonic cellular proliferation during early gestation by ethanol or acetaldehyde (Brown et al., Science 206:573–575 [1979]). However, there may also be selective fetal malnutrition due to placental injury (See Fisher and Karl, Recent Dev. Alcohol., 6:277–289 [1988]).

Current evidence suggests that the average daily consumption of two drinks per day or periodic binge drinking early in pregnancy, may be associated with recognizable abnormalities in a significant percentage of newborns. The smallest quantity of ethanol ingestion reported to be associated with FAS is approximately 75 ml (e.g., approximately 2.5 ounces) per day (See, Rall, supra). FAS children are usually born to women with chronic alcoholism. The effects of excessive ethanol ingestion during pregnancy include stillbirths and spontaneous abortions, which occur two to three times more frequently in women having three or more drinks per day, as compared to women who have less than one drink per day (See, Rail, supra).

One recent estimate suggests that as many as 0.5% of American children may have developmental problems related to maternal ethanol use during pregnancy (A. M. Rudolph (ed.), *Rudolph's Pediatrics,* 20th ed., Appleton & Lange, Stamford Conn. [1995]). Reports indicate that, depending upon the population studied, the incidence of full-blown FAS ranges from 1 in 300, to 1 in 2000 live births; for infants of alcoholic mothers, the incidence is 1 in 3 (See Rall, supra).

Diagnosis of FAS and FAE

Despite the high numbers of affected infants, many physicians are unable to recognize the often subtle features associated with FAS and fail to diagnose it (Lewis et al., "Fetal Alcohol Syndrome" American Family Physician 50:1025–1032 [1994]). Early diagnosis of FAS or FAE is difficult due to the lack of objective indicators and diagnostics. As recommended by the Research Society on Alcoholism, the diagnosis of FAS requires confirmation of a history of maternal alcohol abuse and that the following criteria be met on examination of the child: a) prenatal or postnatal growth retardation (height and weight below the 10th percentile for the gestational age) b) CNS dysfunction (any neurological abnormality, developmental delay, or intellectual impairment; and c) characteristic craniofacial abnormalities, including at least two of microcephaly, microphthalmia or short palpebral features, and poorly developed filtrum, thin upper lip, and flattening of the maxillary area (See e.g., Spohr et al., Lancet, 341:8850 [1993]).

Diagnosis of FAS and "Fetal Alcohol Effects" (FAE), a term used to denote children who have some but not all of the physical characteristics of FAS, is made clinically and based on a maternal history of alcohol consumption during pregnancy. Because this history is difficult to obtain, the true incidence of these conditions may be grossly underestimated. Indeed, some studies have shown a 100% failure to diagnose FAS or FAE. While the most severe case can be diagnosed at birth, in many cases the subtle signs of FAE may not become apparent until children reach school age. Learning difficulties and hyperactivity may be particularly troublesome to both children and parents if the source is not apparent.

The ability to recognize FAS varies according to the physician's skills and interests. While the diagnosis is easier with a known maternal history of alcohol abuse, there are many confounding variables such as reluctance to admit to and accurately report alcohol use, nutritional status, and other substance abuse, which make it difficult to interpret data regarding the relationship between the amount of alcohol consumed and FAS and FAE. Thus, FAS and FAE remain greatly under-diagnosed today, and early intervention is largely therefore precluded.

Treatment of FAS

There is no specific cure for FAS. Treatment generally consists of supportive care and obtaining appropriate services to meet the individual needs of affected children. Therapeutic interventions may be necessary for children with behavioral problems and sensory deficits Dental caries are common in these children, so good dental health is essential. This is particularly important because dental problems can potentiate the feeding and speech problems that frequently occur. Recurrent serous otitis media (ie., middle ear infections) often necessitates multiple myringotomies (i.e., incisions made in the tympanic membrane), and insertion of tympanic membrane tubes. In addition, special educational problems are beneficial for these children. IQ testing during early school age years is recommended as well as consultation with a pediatric dysmorphologist or developmental specialist to facilitate appropriate academic placement. Fortunately, the cardiac septal defects associated with FAS usually close spontaneously and rarely require surgical intervention. Nonetheless, the early recognition of the teratogenic effects of alcohol and intervention is crucial. Thus, what is needed is a reliable diagnostic method for the screening of neonates for exposure to alcohol in utero, in order to facilitate early intervention against the effects of FAS or FAE.

SUMMARY OF THE INVENTION

The present invention relates to methods for detecting teratogen exposure, and in particular for detecting prenatal exposure to alcohols in the neonate. In accordance with the present invention, prenatal exposure to ethanol is determined by extraction and purification of fatty acid ethyl esters from meconium. It is not intended that the present invention be limited by the mechanism by which the fatty acid ethyl esters are determined.

The present invention provides methods for detecting at least one fatty acid ethyl ester of at least one teratogen present in a sample. In one embodiment, the present invention provides a method of detecting at least one fatty acid ethyl ester of at least one teratogen in a sample suspected of containing a fatty acid ethyl ester, comprising the steps of: providing a meconium sample, at least one solvent; and a column comprising a non-amine packing; contacting the sample with the solvent under conditions such that an extracted sample is produced; applying the extracted sample to the column; and eluting the fatty acid ethyl esters from the column.

In a preferred embodiment, the solvent is selected from the group consisting of acetone and hexane. In an alternative preferred embodiment the eluting is accomplished by applying hexane:ethyl acetate to the column. In a particularly preferred embodiment, the sample is from a neonate suspected of suffering from fetal alcohol syndrome.

In one embodiment, the teratogen is selected from the group consisting of ethanol, methanol, propanol, 1-propanol, 2-propanol, butanol, pentanol, octanol, bromoethanol, chloroethanol, dichloroethanol, trichloroethanol. In a preferred embodiment, the teratogen is ethanol.

In a preferred embodiment, the method comprises the further step of analyzing the eluted fatty acid ethyl esters by gas chromatography. In an alternative preferred embodiment, the method comprises the further step of analyzing the fatty acid ethyl esters by gas chromatography-mass spectroscopy.

The present invention also provides methods for detection of at least one fatty acid ethyl ester of at least one teratogen in a sample, comprising the steps of providing a meconium sample, a miscible solvent, an immiscible solvent, and a silica gel column; contacting the sample with the miscible and immiscible solvent under conditions such that an extracted sample is produced; applying the extracted sample to the silica gel column; and eluting the fatty acid ethyl esters from the silica gel column.

In one preferred embodiment, the miscible solvent comprises acetone. In an alternative preferred embodiment, the immiscible solvent comprises hexane. In yet another preferred embodiment, the miscible solvent comprises acetone and the immiscible solvent comprises hexane. In an alternative embodiment, elution is accomplished by applying hexane:ethyl acetate to the silica gel column.

In a particularly preferred embodiment, the sample is from a neonate suspected of suffering from fetal alcohol syndrome. It is contemplated that various samples be used with the methods of the present invention, including meconium, cord blood, etc. However, in preferred embodiments, meconium is used.

In one embodiment, of the method, the teratogen is selected from the group consisting of ethanol, methanol, propanol, 1-propanol, 2-propanol, butanol, pentanol, octanol, bromoethanol, chloroethanol, dichloroethanol, trichloroethanol. In a preferred embodiment, the teratogen is ethanol.

In another preferred embodiment, the method further comprises the step of analyzing the fatty acid ethyl esters by gas chromatography. In an alternative preferred embodiment, the method further comprises the step of analyzing the fatty acid ethyl esters by gas chromatography-mass spectroscopy.

The present method also provides a method of detecting at least one fatty acid from at least one teratogen in a sample comprising the steps of: providing a meconium sample, acetone, hexane, a column, hexane:ethyl acetate, and a gas chromatography column; contacting the sample with the acetone and hexane, under conditions such that an extracted sample is produced; applying the extracted sample to the column; eluting the fatty acid ethyl esters from the column with the hexane:ethyl acetate; and analyzing the fatty acid ethyl esters by gas chromatography.

In a preferred embodiment of the method, the sample is from a neonate suspected of suffering from fetal alcohol syndrome. In an alternative embodiment, the neonate's mother is tolerant to ethanol. However, it is not intended that the method be limited to the tolerance or intolerance of the neonate's mother to ethanol.

In one embodiment, the column is a silica gel column. In a preferred embodiment, teratogen is selected from the group consisting of ethanol, 1-propanol, 2-propanol, butanol, pentanol, octanol, bromoethanol, chloroethanol, dichloroethanol, trichloroethanol. In a particularly preferred embodiment, the method comprises the further step of analyzing the fatty acid ethyl esters by gas chromatography-mass spectroscopy.

DESCRIPTION OF THE INVENTION

Figure 1:
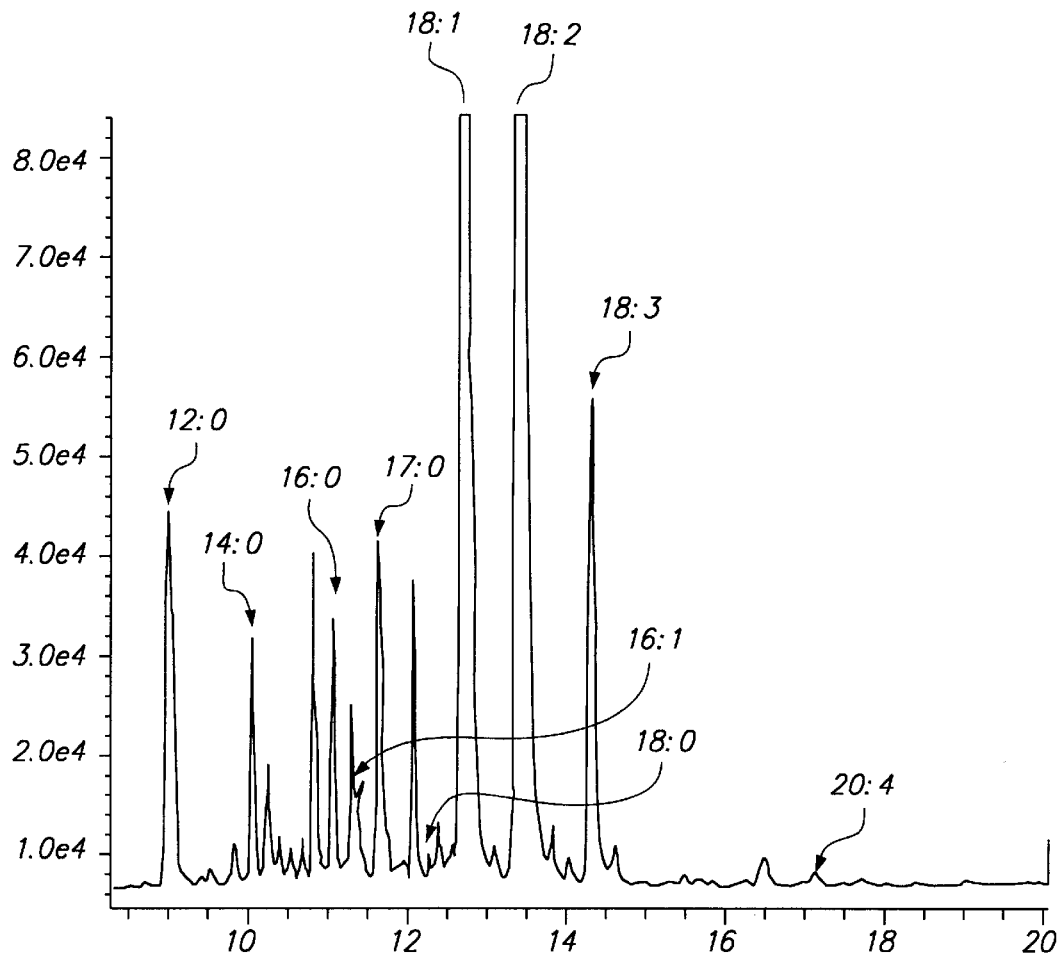
FIG. 1 is a GC chromatogram of a meconium sample strongly positive for the presence of FAEEs (1450 nmoles/g).

The present invention relates to methods for detecting teratogen exposure, and in particular for detecting prenatal exposure to alcohol in the neonate. The present invention provides rapid and simple methods for the detection and analysis of fatty acid ethyl esters (FAEEs) obtained from samples obtained at birth. Although various samples may be tested using the methods of the present invention, the use of meconium samples as described below has many advantages, including the fact that the samples may be collected by non-invasive methods. The detection of FAEEs as the basis to diagnose neonates suffering from FAS is based on the recognition of the pathways of alcohol metabolism, and the identification of FAEEs as a useful diagnostic tool.

I. Alcohol Metabolism and Fatty Acid Ethyl Esters as Biomarkers for Alcohol Exposure In mammals, alcohol is metabolized primarily in the liver, via two different pathways, namely, the oxidation of ethanol to acetaldehyde by either alcohol dehydrogenase (ADH), or the microsomal ethanol-oxidizing system. Ethanol may be oxidized by alcohol dehydrogenase and the microsomal oxidizing system to generate acetaldehyde, which in turn is further oxidized to acetate by aldehyde dehydrogenase. Ethanol can also be metabolized in a non-oxidative fashion and esterified with a fatty acid to form fatty acid ethyl esters in a reaction catalyzed by numerous enzymes including triglyceride lipase and carboxylesterase. The enzyme activity is frequently referred to as fatty acid ethyl ester synthase.

Non-oxidative ethanol metabolism to produce fatty acid ethyl esters (FAEE) has been recently described and has been observed in both liver and extrahepatic tissues (See e.g., Bearer et al., supra). In addition, the non-oxidative pathway has been described in fetal and placental tissues (See e.g., Bearer et al., supra). The synthesis and accumulation of FAEE following ethanol ingestion has been shown in human pancreas, liver, adipose tissue, heart, bone marrow, peripheral white blood cells, cerebral cortex, skeletal muscle, and the aorta. It is possible that this synthesis and accumulation of FAEE may represent a mechanism for ethanol-induced damage or toxicity in organs lacking ADH. Indeed, the organs most frequently damaged by ethanol abuse have been shown to contain the highest levels of FAEE synthase activity and after acute intoxication, the highest level of FAEEs. Thus, the presence of FAEEs following ethanol ingestion, as well as the enzyme activity responsible for their synthesis provides circumstantial evidence that FAEEs are toxic metabolites which may account in part for ethanol induced organ damage (Doyle et al., J. Lipid Res., 35:428–437 [1994]).

Specific laboratory tests can be used to identify individuals (ie., adults) who are alcohol dependent. For example, the laboratory values of a number of biological markers, such as carbohydrate-deficient transferrin are often elevated in cases of chronic and acute alcohol abuse (Lesch and Walter, Alcohol & Alcoholism 31:59–62 [1996]).

FAEEs have been suggested as potential markers for alcohol exposure in adults. For example, Laposata et al. suggested that FAEEs isolated from adipose tissue may be useful as a marker of chronic ethanol ingestion (E. A. Laposata et al., Arch. Pathol. Lab. Med., 113:762–766 [1989]). Similarly, FAEE's have been isolated from adult heart, liver and serum in studies of the pathophysiology of alcoholism (P. M. Kinnunen and L. G. Lange, Anal. Biochem., 140:567–576 [1984]; and P. S. Bora and L. G. Lange, Alcohol. Clin. Exp. Res., 17:28–30 [1993]).

Fatty acid ethyl esters have also been shown to be present in mouse placental and fetal tissues after maternal ethanol exposure (C. F. Bearer et al., supra). Infant cord blood samples have also been shown to contain FAEE's and their use has been suggested as a marker for prenatal alcohol exposure (C. F. Bearer et al., Pediatr. Res., 68A [1992]). Indeed, TLC has been used to extract FAEEs from a cord blood specimen obtained at birth from a neonate born to an alcoholic woman, as described by Bearer et al, Pediatr. Res., 31:492–495 [1995]. GC was used to characterize the FAEE components, and GC/MS was used to confirm the GC results. In contrast to the sample obtained from the neonate born to the alcoholic mother, a cord blood specimen obtained from a healthy control was also tested, and found to contain no significant accumulation of FAEEs.

In addition, Mac et al. reported the identification of FAEEs in meconium of alcohol exposed infants through use of thin layer chromatography (TLC) or column chromatography (i.e., aminopropyl columns)(E. Mac et al., Pediatr. Res., 35:238A [1994]). However, the present invention provides the first method for FAEE analysis in samples obtained at birth (e.g., meconium) that is reproducible and reliable. While it is not intended that the present invention be limited to the use of any one method, the present invention provides the first method for FAEE analysis using silica gel columns. Indeed, the present invention provides rapid and simple methods for the detection and analysis of FAEEs obtained from samples obtained at birth.

II. Extraction and Purification of Fatty Acid Ethyl Esters from Neonatal Samples The present invention contemplates extraction and quantification of fatty acid ethyl esters from neonates. In particular, it is contemplated that meconium and cord blood will be used with the present invention as fatty acid ethyl esters may be detected in these samples, and provide a non-invasive approach to testing for prenatal alcohol exposure. In one embodiment, the present invention provides methods for the extraction of FAEE from meconium with water/acetone/hexane, purification by chromatography and quantification by comparison to an internal standard of heptadecanoic ethyl ester.

In contrast to the present invention, Kinnunen and Lange describe a method for the extraction, quantitation and definitive identification of fatty acid ethyl esters formed in adult biological tissues which depends upon their extraction with acetone, isolation by TLC on silica gel developed with an apolar solvent system (ie., petroleum ether:diethyl ether:acetic acid, 75:5:1), and individually identification by GC-Mass spectrometry (Kinnunen and Lange, supra).

Definitions

To facilitate further understanding of the invention, a number of terms are defined below:

The terms "sample" and "specimen" in the present specification and claims are used in their broadest sense. On one hand, they are meant to include a specimen or culture. On the other hand, they are meant to include both biological and environmental samples. These terms encompasses all types of samples obtained from humans and other animals, including but not limited to, body fluids such as urine, blood, cord blood, sputum, fecal matter, cerebrospinal fluid (CSF), semen, and saliva, as well as solid tissue. In particular, the terms encompass samples such as meconium or rectal swabs obtained from neonates. These terms also refers to swabs and other sampling devices which are commonly used to obtain samples.

As used herein, "teratogen" refers to any environmental factor that can cause an abnormality in form or function (ie., birth defects [form] or mental retardation [function]) in an exposed fetus. It is intended that the term encompass any compound or physical effect that may cause fetal abnormalities, in particular fetal exposures that result in the production of abnormalities. Thus, it is not intended that the term be limited to specific compounds such as ethanol.

As used herein, the term "fatty acid" refers to any monobasic aliphatic acid containing only carbon, hydrogen, and oxygen, and consist of an alkyl radical attached to the carboxyl group. The saturated fatty acids have the general formula $C_nH_{2n}O_2$. Methanoic and ethanoic acid are the two lowest members of this series, which includes palmitic acid and stearic acid. There are various series of unsaturated fatty acid. The oleic acid series ($C_nH_{2n-2}O_2$), contains compounds with one double bond; acrylic acid is the lowest member in this series. The linoleic acid series ($C_nH_{2n-4}O_2$) contains compounds with two double bonds. The linolenic acid series ($C_nH_{2n-6}O_2$) contains compounds with three double bonds. Also encompassed are natural and synthetic fatty acids with four or more double bonds, fatty acids containing hydroxy groups, and cyclic fatty acids.

As used herein, the term "ester" refers to organic compounds often formed by the combination of an acid and an alcohol, with elimination of water. Also encompassed within this term are esters produced by the action of an alcohol on an acid chloride or anhydride, or the action of an aldehyde on aluminum ethoxide or isopropoxide. Methyl and ethyl esters may be produced by treating the sodium salt of the acid with methyl or ethyl sulfates. For example, diazomethane may be reacted with organic acids to produce methyl esters, while heating an alcohol with the methyl or ethyl of the acid can be used to produce methanol or ethanol. Esters may be completely hydrolyzed to acid and alcohol by heating in the presence of dilute sodium hydroxide solution. Reactions between esters and ammonia can be used to produce amides.

As used herein, the term "ethyl" refers to the group $CH_3CH_2$ ($C_2H_5$ or "Et—"). Ethyl groups may be present in various compounds including but not limited to, "ethyl alcohol" (i.e., "ethanol") which has the formula $CH_3CH_2OH$, and ethyl amines (e.g. monoethylamine $[CH_3CH_2NH_2]$).

As used herein, the term, "fatty acid esters" is intended to include, but is not limited to fatty acid esters of xenobiotics including, 2-chloroethanol (e.g. 16:0, 10:0, 12:0, 14:0, 18:0, and 18:2), carbofuran (e.g., 5:2), pentachlorophenol (e.g., 16:0), and 3-chloro-1,2-propanediol (e.g., 16:0, and 18:0). It is also intended that the term encompass fatty acid esters of aliphatic and halogenated alcohols formed in vivo and in vitro, including but not limited to ethanol (e.g., 14:0, 16:0, 16:1, 18:0, 18:1, 18:2, 18:3, and 20:4), 1-propanol (e.g., 12:0, 14:0, 16:0, 18:0), 2-propanol (e.g., 18:1), 1-butanol (e.g., 18:1), 1-pentanol (e.g., 18:1), 3-methyl-1-butanol (e.g., 18:1), 1-octanol (e.g., 18:1), 2-chloroethanol (e.g., 16:0, 18:0, 18:1, 16:0, 18:0, 18:1, 18:2, 18:3, and 20:4), 2-bromoethanol (e.g., 16:0, and 18:0), 2,2-dichloroethanol (e.g., 18:1), 2,2,2-trichloroethanol (e.g., 16:0, and 18:1). It is also intended that the term encompass fatty acid esters of pesticides and drugs formed in vivo and/or in vitro, including but not limited to, acaricide (i.e.,2-napthyl methyl cyclopropane carboxylate) and acaricide metabolites (e.g., 2-naphthalenyl-methanol)(.e.g., 16:0, 18:0, 20:0, 22:), fatty acid esters of pentachlorophenol (e.g., 16:0), DDT (2,2-bis-(p-chloro-phenyl)-1,1,1-trichloroethane) and its metabolites, (e.g., DDOH [2,2-bis-(2-chlorophenyl-)-1,1-dichloroethanol]) (e.g., 16:0, 18:0, 18:1, and 18:2), TCHs (tetrahydrocannabinols, including $\Delta^9$-tetrahydrocannibinol $[\Delta^9$-THC], and $\Delta^8$-tetrahydrocannibinol $[\Delta^8$-THC],) and its metabolites (e.g., 11-hydroxy-$\Delta^8$-THC, 11-hydroxy-$\Delta^9$-THC) (e.g., 16:0, 18:0, 18:1, and 18:2), phencyclidine metabolites (e.g. 4-hydroxy-cyclo-phencyclidine)(e.g., 16:0, 18:0, 18:1, and 18:2), codeine (e.g., 16:0, 18:0, 18:1, and 18:2), etofenamate (e.g., 12:0, 14:0, 16:0, 16:1, 18:0, 18:1, and 18:2), plaunotol (e.g., 16:0, 18:0, and 18:1), and chlorambucil (e.g., 20:4, and 22:6).

As used herein, the term "fatty acid ethyl ester" ("FAEE") refers to compounds produced by the reaction of ethanol with free fatty acids. It is intended that the term not be limited to any particular compound nor it is related to any particular method of production, although in one embodiment, FAEEs are produced by enzymatic conjugation.

As used herein, the term "fatty acid amides" is intended to include, but is not limited to such compounds as aniline, cyclohexylamine, N-cyclohexylhydroxylamine.

As used herein, the term "alcohol" refers to any organic compound that contains one or more hydroxyl groups attached directly to a carbon atom. Aromatic derivatives with hydroxyl groups joined directly to the carbon atoms of the ring are referred to as "phenols." Compounds with one hydroxyl (i.e., —OH) group are referred to as monohydric alcohols, while those with more than one are di-, tri-, or poly-hydric alcohols. Aliphatic dihydric alcohols are referred to as "glycols" (e.g., glycerol). Tetra-, penta-, and hexa-hydric alcohols are generally derived from sugars. It is not intended that the present invention be limited to such commonly recognized alcohols as ethanol, methanol, propanol, etc. As used herein, the terms "ethanol" and "ethyl alcohol" refer to the compound with the chemical formula "$CH_3CH_2OH$," commonly ingested by humans.

As used herein, the term "solvent" refers generally, to any chemical compound useful for the removal (ie., extraction) of soluble material from a solid mixture. However, it is not intended that the term be strictly limited to this context, as solvents may be used for the removal of one or more components from a liquid mixture, with which the liquid is immiscible in the solvent. As shown herein, solvent mixtures were prepared by additive combination of the named solvents in the indicated proportions by volume. For example, "isooctane-ethyl acetate 20:1," is a v/v (ie., volume to volume) combination of 20 volume units of isooctane with 1 volume unit of ethyl acetate.

As used herein, the term "miscibility" refers to the extent of mixing that is possible between the combination of two or more compounds or substances. For example, liquids may be completely miscible (e.g., alcohol and water), partially miscible (e.g., aniline and water), or almost completely immiscible (e.g., mercury and water). The miscibility of liquids is dependent upon their physical and chemical properties.

As used herein, the term "column" refers to a chromatographic column that is filled with "packing," "packing material," or "matrix," or "resin." It is contemplated that various packing materials will be used in the column. For example, it is contemplated that silica gel, C18, and other compounds will be used as packing materials in the column of the present invention. It is not intended that the type of column be limited to a particular format. For example, it is contemplated that the commercially available materials such as those provided by Alltech will be used in the present invention, including but not limited to Adsorbosil, Adsorbosphere, Alltima, Econosil, Econosphere, hydroxyethyl methacrylate polymer (HEMA), macrosphere 300, C18/anion, C18/cation, Tenax-TA, Tenax-GC, "amine packings" (e.g., column materials commercially available from suppliers such as Alltech, including, Alltech Amine Packing, Carbowax®, Carbowax® 20M, Porapak®, HayeSep®, Chromosorb®, Amipack®, Apiezon®, and AT™-WAX), DB™-WAX, Superox® II, HP-20M, Supelcowax®-10, and Versapack materials. Thus, as used herein, the term "non-amine packing" therefore, includes packing materials other than aminopropyl and other packings listed above as "amine packings," yet encompasses packings including but not limited to silica and C18, as well as other packings. It is not intended that the column packing materials be limited to a specific supplier or composition.

As used herein, the term "silica gel" refers to a gel substance comprised of silica. In particular, the term refers to a column chromatography material comprised of silica.

As used herein, the term "hydrophobic resin" refers to column resins that are hydrophobic. For example, the term is intended to encompass such packing materials as C18 (indicated as being hydrophobic by Margois-Nunno and Horowitz, PCT Publ. No. WO 95/00631, page 11), As used herein, the term "reversed phase" refers to packings such as C18, C8, C2, cyclohexyl and phenyl bonded phases, and XAD-2 resins. As used herein, the term "normal phase" refers to silica, florisil, amino, cyano, diol, and alumina packings. As used herein, the term "ion exchange" refers to strong anion (e.g., SAX) and cation (SCX) exchangers. It is intended that these terms encompass packings that have been modified by any number of procedures. For example, the packing may be modified by adding an appropriate solvent to increase or decrease its polarity.

As used herein, the term "elution" refers to the process of separating a material into its components by washing or running the material on a chromatography column.

As used herein, the term "elutriation" refers to the purification of a substance by dissolving it in a solvent, pouring off the solution As used herein, the term "eluate" refers to the components removed by or the product of elution or elutriation.

As used herein, the term "eluent" refers to the solution (i.e., liquid or fluid) used in elution.

As used herein, the term "gas chromatography" refers to the method in which a volatile sample is introduced into a gas chromatography column, eluted from the column, and detected and identified based upon its retention time within the column, as compared to known standards.

As used herein, the term "gas chromatography-mass spectroscopy" refers to the method by which gas chromatography is combined with mass spectroscopy. In this method, a compound or substance is separated by gas chromatography into its various components that are visualized as "peaks" on a chromatogram. Mass spectroscopy is then used to establish the identity of the substance at each peak. This is achieved by the conversion of the compound present in each peak into electrically charged ion fragments. As each compound breaks down into different fragments that may be distinguished from the fragments obtained by the break down of other compounds, the pattern of fragments obtained provides an identification of the compound. A computer is used to compare the fragment pattern obtained with the test compound or substance with the patterns of known substances or compounds.

As used herein, the term "meconium" refers to the waste products which accumulate as the intestinal contents of fetuses during gestation. Meconium, usually a dark-colored, mucilaginous mass, is comprised of desquamated intestinal and skin epithelial cells, pancreatic and intestinal secretions, and residue of swallowed amniotic fluid. Unlike urine, which is excreted from the fetus in utero, meconium is not normally excreted until after birth.

As used herein, the term "cord blood" refers to blood obtained from the umbilical cord.

EXPERIMENTAL

The following examples serve to illustrate certain preferred embodiments and aspects of the present invention and are not to be construed as limiting the scope thereof. Unless otherwise indicated, the solvents and alcohols used in these Examples were obtained from Fisher. Also, unless otherwise indicated the solvents and alcohols used herein were HPLC grade.

In the experimental disclosure which follows, the following abbreviations apply: eq (equivalents); M (Molar); $\mu M$ (micromolar); N (Normal); mol (moles); mmol (millimoles); $\mu mol$ (micromoles); nmol (nanomoles); pmol (picomoles); gm or g (grams); mg (milligrams); $\mu g$ (micrograms); L (liters); ml (milliliters); $\mu l$ (microliters); cm (centimeters); mm (millimeters); $\mu m$ (micrometers); nm (nanometers); xg (times gravity); °C. (degrees Centigrade); GC-MS and GC/MS (gas chromatography-mass spectroscopy); FAEE (fatty acid ethyl ester); mixed FAEE (C 12:0, 14:0, 16:0, 16:1, 18:0, 18:1, 18:2, 18:3, and 20:4; Sigma); Alltech (Alltech Deerfield, Ill.); Sigma (Sigma Chemical Co., St. Louis, Mo.); and Fisher (Fisher Scientific, Pittsburg, Pa.).

EXAMPLE 1

Preparation of Silica Columns

In this Example, the silica gel was prepared by placing one volume of silica gel (EM Science CAS 63231-67-4) into a glass beaker. The silica gel was washed with HPLC grade methanol (Fisher), the gel allowed to settle, and the methanol decanted. This methanol wash was repeated three times. The gel was allowed to dry overnight in a fume hood. The silica gel was then resuspended in HPLC grade isooctane (Fisher), and placed in a side arm flask. The openings of the sidearm and flask were covered with aluminum foil, and stored at room temperature until use.

The columns were prepared by first washing 5" borosilicate Pasteur pipettes in HPLC grade acetone, and allowed to dry. A small pellet of glass wool was then packed into the barrel of each pipette. The silica gel prepared as described above, was degassed with nitrogen gas, at 30° C., for five minutes in an evaporator. After degassing, the gel was gently swirled, to produce a slurry. This slurry was then poured into the glass wool-packed Pasteur pipettes, until the height of the packed silica gel was approximately 5 cm., and packed in the barrel of the pipettes. The packed material in each pipette was then washed five times with 1 ml aliquots of hexane.

EXAMPLE 2

Identification of Optimum Solvent for Use with Silica Gel

In this Example, various solvent systems were tested for their ability to extract FAEE from samples run on silica gel columns.

Silica gel was selected for this Example, as it has been used to separate various classes of lipids (See e.g., S. T. Ingalls et al. "Method for isolation of non-esterified fatty acids and several other classes of plasma lipids by column chromatography on silica gel," J. Chromatogr., 619:9–19 [1993]). Initially, the solvent systems described by Ingalls et al. were tested with 17:0 EE (1 mM 17:0 heptadecanoic ethyl ester). For each of three experiments, four 1 ml aliquots of each solvent were added, and the eluates were collected separately. Each fraction was dried under nitrogen and analyzed by GC/FID as described in Example 3. The results are shown in Table 1.

TABLE 1

| | Results of Four Solvent Systems | | |
| --- | --- | --- | --- |
| | Experiment #1 (% Recovery) | Experiment #2 (% Recovery) | Experiment #3 (% Recovery) |
| Solvent 1 | Isooctane:ethyl acetate 80:1 (100) | Isooctane (100) | Hexane (0) |
| Solvent 2 | Isooctane:ethyl acetate 60:1 (0) | Isooctane:ethyl acetate 160:1 (0) | Hexane:ethyl acetate 160:1 (0) |
| Solvent 3 | Isooctane:ethyl acetate 40:1 (0) | Isooctane:ethyl acetate 100:1 (0) | Hexane:ethyl acetate 100:1 (100) |

TABLE 1-continued

| | Results of Four Solvent Systems | | |
| --- | --- | --- | --- |
| | Experiment #1 (% Recovery) | Experiment #2 (% Recovery) | Experiment #3 (% Recovery) |
| Solvent 4 | Isooctane:ethyl acetate 20:1 (0) | Isooctane:ethyl acetate 80:1 (0) | Hexane:ethyl acetate 80:1 (0) |

As shown in Table 1, in the initial experiment (Experiment #1), 17:0 EE was not retained. Based on this result, in Experiment 2, the solvent system was adjusted to lessen the elutropic power, by decreasing the amount of ethyl acetate. However, the 17:0 EE was still not retained by the column. Thus, Experiment 3 was designed to decrease the elutropic power even further by replacing the isooctane with hexane. As shown in Table 1, the new solvent system with hexane:ethyl acetate, was found to successfully retain the 17:0 EE to the third fraction. In subsequent experiments (See e.g., Example 3) with meconium and serum as samples, the purity of the FAEE was confirmed. By separate GC/MS analysis, the identity of the FAEE was confirmed.

EXAMPLE 3

Identification of Optimum Solvent(s) and Column Resin(s)

In this Example, various solvents were tested for their ability to extract FAEE from samples using columns comprised of three different resins. The three column resins tested included silica (prepared as described in Example 1), aminopropyl, and C18. The aminopropyl column and method used in this Example were those described in the abstract and poster presentation of Mac (Mac et al, et al, Pediatr. Res., 35:238A [1994]).

The aminopropyl and C18 columns were obtained from Alltech. For each column type (aminopropyl, C18, and silica), three different solvent systems were compared for their ability to recover added (or "spiked") FAEE from samples, and their ability to purify FAEE. Nine solvent formulations, divided into three "Solvent Systems" were tested on each of these columns, including 100% hexane, hexane:ethyl acetate (160:1), hexane:ethyl acetate (100:1), 100% isooctane, isooctane:ethyl acetate (160:1), isooctane:ethyl acetate (100:1), 100% methanol, methanol:ethyl acetate (160:1), and methanol:ethyl acetate (100:1). Solvent System I consisted of hexane, hexane:ethyl acetate 160:1, and hexane:ethyl acetate 100:1; Solvent System II consisted of isooctane, isooctane:ethyl acetate 160:1, and isooctane:ethyl acetate 100:1; and Solvent System III consisted of methanol, methanol:ethyl acetate 160:1, and methanol:ethyl acetate 100:1.

Each of the columns tested was initially equilibrated in the starting solvent (ie., hexane, isooctane, or methanol), by washing packed columns with 4 ml of solvent. An aliquot of internal standard, comprised of 17:0 ethyl ester (1 mM heptadecanoic ethyl ester), was dried under nitrogen, resuspended in 1 ml of the appropriate starting solvent, and added to the column, and the eluant collected. The column was washed with four 1 ml aliquots of the same solvent, and the eluant was collected in the same test tube. The combined 5 ml were referred to as "hexane," "isooctane," or "methanol."

Next, four 1 ml aliquots of the second solvent (ie., the 160:1 mixes of ethyl acetate) were added to the column, the eluates were collected and combined into one tube. The combined 4 ml fractions were called "hexane:ethyl acetate 160:1," "isooctane:ethyl acetate 160:1," or "methanol:ethyl acetate 160:1."

Next, four 1 ml aliquots of the third solvent (the 100:1 mixes of ethyl acetate) were added to the column, the eluates were collected and combined into one tube. The combined 4 ml fractions were called "hexane:ethyl acetate 100:1," "isooctane:ethyl acetate 100:1," or "methanol:ethyl acetate 100:1."

All of the collected fractions were evaporated to dryness under nitrogen at 30° C., resuspended in 200 µl hexane, and analyzed by GC with a flame ionization detector (GC/FID). The percent recovery of 17:0 ethyl ester was calculated for each fraction. These results are shown in Table 2. In this Table, the results are expressed as the percentage recovery of the FAEE in the internal standard (17:0 EE). As indicated in this Table, fatty acid ethyl esters did not adhere to the aminopropyl columns (i.e., the standard came through the column in all three Solvent Systems), indicating that this column resin was unsuitable for use in the present invention with hexane, isooctane or methanol. This is in contrast to the report of Mac et al. in their abstract, supra and poster.

For Solvent System I, the percent purity of the FAEE extracted from meconium and run on each of the three columns was also determined. Meconium known to contain no FAEE was spiked with the mixed FAEE standard (i.e., 17:0 EE). This sample was subsequently extracted, isolated, and run on GC. Then, the peak areas of all the peaks and the peak areas corresponding to when just the FAEE mixed standard was run on GC were summed. The percent purity of the FAEE extracted from the spiked meconium was calculated as the sum of the peak areas of the FAEE standard, divided by the sum of the total peaks, and then multiplied by 100. Thus, the higher the percentage purity of FAEE, the fewer the number of other peaks observed.

For the aminopropyl column, the percent purity of the FAEE obtained using 100% hexane as the solvent was 4.7%; for the silica column, the percent purity of the FAEE obtained using hexane:ethyl acetate (100:1) as the solvent was 51.3%; and for the C18 column, the percent purity of the FAEE obtained using hexane:ethyl acetate (100:1) as the solvent was 57%.

TABLE 2

Solvents and Column Resins
(Percent Recovery of 17:0 EE Internal Standard)

| | Solvent System | Silica | Aminopropyl | C18 |
|---|---|---|---|---|
| Solvent System I: | Hexane | 0 | 104 | 0 |
| | Hexane:Ethyl Acetate 160:1 | 0 | 5.2 | 0 |
| | Hexane:Ethyl Acetate (100:1) | 103.6 | 0 | 111.4 |
| Solvent System II | Isooctane | 0 | 94.4 | 0 |
| | Isooctane:Ethyl Acetate (160:1) | 0 | 9.2 | 0 |
| | Isooctane:Ethyl Acetate (100:1) | 67.2 | 0 | 116 |
| Solvent System III | Methanol | 70.5 | 104.9 | 111.3 |
| | Methanol:Ethyl Acetate(160:1) | 0 | 0 | 0 |
| | Methanol:Ethyl Acetate (100:1) | 0 | 0 | 0 |

EXAMPLE 4

FAEE Extraction from Meconium

In this Example, FAEEs were extracted from meconium. First, a water-miscible solvent, acetone, was used to extract the meconium. Then, the FAEEs were separated from the acetone through use of a solvent that is immiscible in water, hexane.

In this Example, mixed standards were prepared by adding 100 µl of mixed ethyl esters and 100 µl of 1 mM 17:0 heptadecanoic ethyl ester internal standard into GC vials fitted with glass inserts, capped tightly, and vortexed for one minute at a speed setting of 3–4. The vortexing was accomplished so as to create full swirling.

One gram of the meconium sample obtained from a healthy neonate was added to a 30 ml Corex tube that had been pre-washed with acetone. One ml of distilled water was added to the Corex tube. The internal standard (100 µl of 1 mM 17:0 heptadecanoic ethyl ester) was added to the sample. The tube was thoroughly vortexed for approximately one minute at a speed setting of 3–4, again to create full swirling.

Three ml of acetone was added to the meconium sample in the Corex tube. The meconium was mixed into the acetone with a spatula until it became dry and fibrous. The spatula was rinsed using 2 ml of acetone and the rinse placed in the tube. The tube was vortexed for one minute at a speed setting of 3–4, after which 5 ml of hexane was added. The tubes were then vortexed for 1 minute at a speed setting of 1–2, and then centrifuged for 5 minutes at 800×g.

The top layer, containing the hexane phase was transferred to a clean, acetone-washed Corex tube and stored at room temperature. An additional 5 five ml of hexane were added to the meconium/acetone/water mixture, the tube was vortexed for 1 minute at a speed setting of 1–2, and then centrifuged for 5 minutes at 800×g. The top layer (i.e., the hexane phase) was added to the Corex tube containing the first hexane phase collected. The bottom, aqueous layer was discarded.

The hexane phase was dried under nitrogen gas, at 30° C., until complete dryness. The dried sample was then resuspended in 1 ml hexane, vortexed for 15 seconds at a speed setting of 1–2, and added to the silica gel column prepared according to the method of Example 1. The flow-through from the silica gel column was collected in a test tube. The column was then washed four times with 1 ml hexane. The wash was collected in the same test tube as the flow through, and saved until the GC results were analyzed to show that FAEEs did not pass through the column during the wash steps.

A fresh solution of hexane:ethyl acetate 160:1 was then prepared. Four 1 ml aliquots were added to the column, and the eluant was collected in one test tube and stored.

A fresh solution of hexane and ethyl acetate (100:1) was then prepared. This solution was then used to elute the FAEEs from the column. This elution was conducted five times with 1 ml aliquots. The total 5 ml eluate was collected in a clean test tube. If any of this 100:1 eluate dripped on the side of the collection tube, the tube sides were washed with 0.4 ml hexane and the wash collected into a tube. If any silica gel was present in the eluate, the purification was repeated by running all of the washes through a new silica gel column.

The eluate (5 ml) was dried down under nitrogen gas until complete dryness. The sample was resuspended with 200 µl hexane, ensuring that the sides of the test tube were rinsed. The sample was then vortexed for 15 seconds at a speed setting of 1. The sample was transferred to a GC vial and tightly capped. These steps were determined to be time-sensitive, due to the possibility of hexane evaporation. If hexane evaporation occurs, higher concentrations than expected will result. Thus, it is critical that the steps are quickly and consistently performed for each sample, with one sample being processed at a time (i.e., all of the samples should not be resuspended and transferred at once).

The GC was loaded with the sample. For each run, the GC was loaded with a hexane standard, a mixed FAEE standard, and a 17:0 FAEE standard, as well as the samples. FAEE were clearly identified in some, but not all meconium samples. Nonetheless, recovery of the internal standard from the meconium was >90%, for all samples. Based on these analyses, the amount of FAEE in meconium was calculated, with the limit of detection being approximately 1 pmol/g wet weight meconium.

Figure 2:
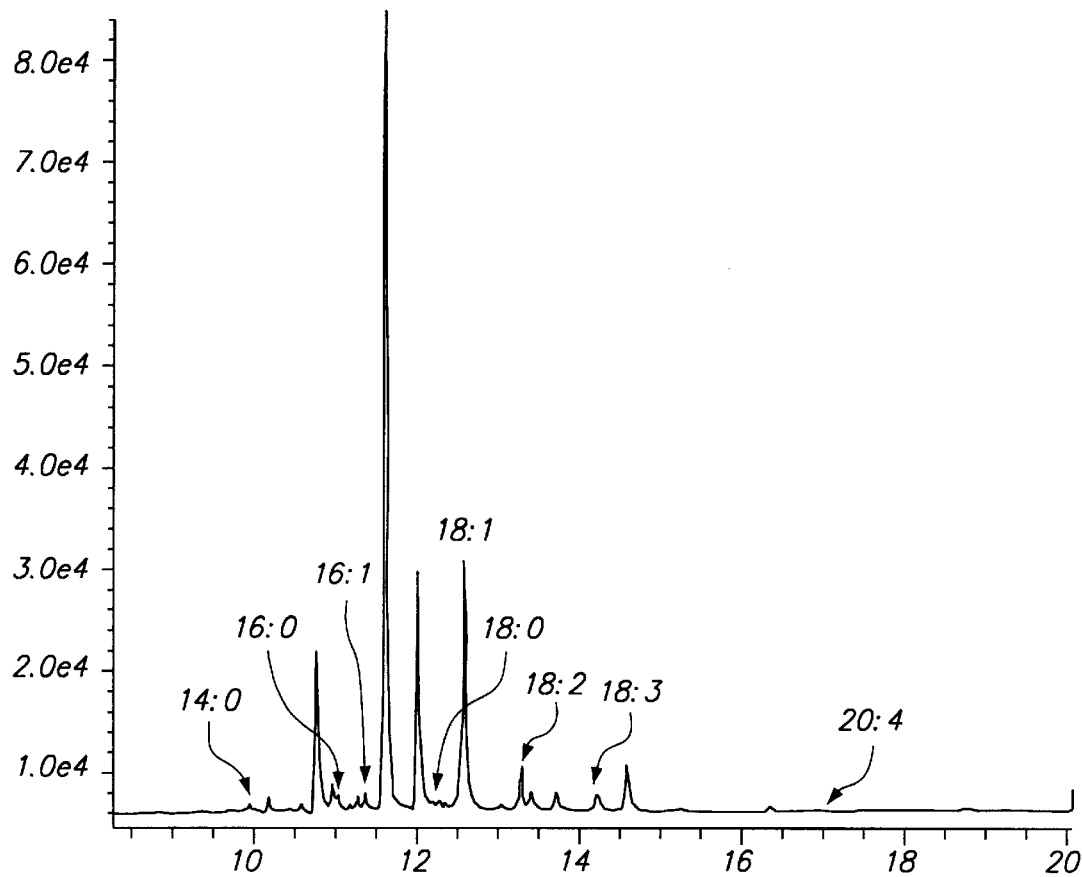
FIG. 2 is a GC chromatogram of a meconium sample that was positive for the presence of FAEEs (10 nmoles/g).
Figure 3:
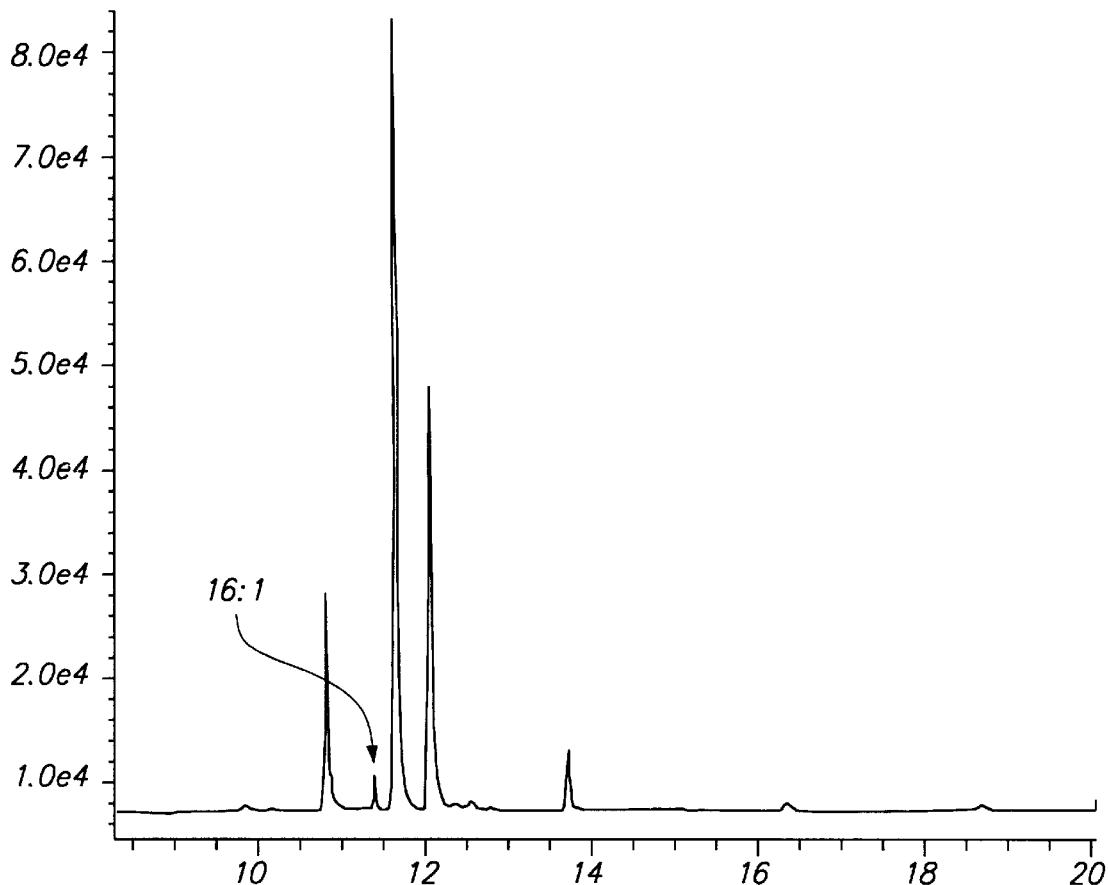
FIG. 3 is a GC chromatogram of a meconium sample that was negative for the presence of FAEEs.

FIGS. 1–3 show the GC results obtained with three meconium samples. As shown in FIG. 1, FAEE were clearly identified in this meconium sample. This was a strongly positive sample, with 1450 nmol/g FAEE detected. FIG. 2 is a chromatogram from a sample that was positive for FAEE (10 nmol/g), while FIG. 3 is a chromatogram of a sample that was negative for FAEE.

EXAMPLE 5

Detection of Other Solvents

In this Example, the methods of previous Examples were used to test whether exposure to compounds such as industrial solvents could be detected. Palmitate propyl ester (16:0 PE) was chosen for this experiment as propanol is a commonly used solvent, and has been shown to be conjugated to palmitate to form palmitate propyl ester in a number of tissues from experimental animals (See e.g., G. P. Carlson, "In vitro esterification of fatty acids by various alcohols in rats and rabbits," Toxicol. Lett., 70:57–61 [1994]; and G. P. Carlson, "Formation of fatty acid propyl esters in liver, lung and pancreas of rats administered 1-propanol," Res. Commun. Chem. Pathol. Pharmacol., 81:121–124 [1993]).

Initially, 100 µl of 0.1 mM 16:0 PE was dried under nitrogen gas, resuspended in 1 ml hexane, and then applied to silica columns prepared as described in Example 1. The 16:0 PE was eluted from the silica columns as described in Example 5. Specifically, the following solvents were applied and collected: 4 ml hexane, 4 ml hexane:ethyl acetate 160:1, and 5 ml hexane:ethyl acetate 100:1. The results are shown in Table 3.

Subsequently, 100 µl of 16:0 PE was added to a meconium sample from a healthy neonate, and then extracted as described in Example 5. Two runs were tested for both the standard and 16:0 PE-spiked meconium samples. These results are also shown in Table 3 (each run is indicated as #1 or #2, for either the standard or test samples).

As shown in Table 3, the best solvent for recovering 16:0 PE from the meconium was hexane:ethyl acetate 100:1.

EXAMPLE 6

Rapid Detection of FAEE

Absorbance at 206 nm is a sensitive simple assay to detect unsaturated fatty acids from the column fraction. Therefore, experiments were conducted to establish whether it is possible to use UV absorption rather than GC/FID GC-MS to confirm the identity of fatty acids present in samples such as meconium.

In this experiment, either a standard of 100 µl of 1 mM ethyl linoleate (18:2 EE) solution, or an extract of meconium was applied to silica columns and the FAEE isolated as described above (See, Examples 1–4). The 100 µl hexane:ethyl acetate fraction was evaporated with nitrogen gas to dryness, as described above, and then resuspended in 3 ml hexane. The $OD_{206}$ was then measured spectrophotometrically.

The initial experiments showed a linear response of $OD_{206}$ to 18:2 EE concentration. Subsequent tests showed a high $OD_{206}$ absorption of the 100:1 fraction obtained from a GC-negative meconium sample. The increase in absorption observed that was not related to the presence of FAEE may be due to either background chemicals in the 100:1 fraction, or contamination with the silica gel.

In addition to the silica gel columns tested as described above, C18 columns and the solvent systems listed in Table 1 are tested in combination in order to reduce the absorption of negative meconium samples.

EXAMPLE 7

Correlation of FAEE in Meconium and Maternal Alcohol Tolerance

In this Example, the correlation between FAEE in meconium and maternal drinking and tolerance to alcohol was investigated.

In this example, meconium (i.e., the first meconium excreted) samples from 248 neonates enrolled at the time of delivery in a 2-year longitudinal neurobehavioral study were analyzed according to the methods described in the above Examples (See, Example 4). A detailed questionnaire adapted from the Maternal Post-partum Substance Abuse Assessment (See, A. P. Streissguth, "The behavioral teratology of alcohol: Performance, behavioral and intellectual deficits in pre-natally exposed children," in J. R. West (ed.), *Alcohol and Brain Development,* Oxford University Press, New York, pp. 3–44 [1986]; A. P. Streissguth, "Smoking and

TABLE 3

Isolation of Palmitate Propyl Ester

|  | Isolation of 16:0 PE Standard (% Recovery) Run #1 | Isolation of 16:0 PE Standard (% Recovery) Run #2 | Isolation of 16:0 PE From Meconium (% Recovery) Run #1 | Isolation of 16:0 PE From Meconium (% Recovery) Run #2 |
|---|---|---|---|---|
| Hexane | 0 | 0 | 0 | 0 |
| Hexane:ethyl acetate 160:1 | 0 | 0 | 0 | 0 |
| Hexane:ethyl acetate 100:1 | 108.97 | 111.43 | 72.59 | 77.66 | drinking during pregnancy and offspring learning disabilities," in Lewis (ed.), *Learning Disabilities and Prenatal Risk,* University of Illinois Press, Urbana-Champaign, Ill., pp. 28–67 [1986]; and A. P. Streissguth et al., "Intelligence, behavior, and dismorphogeneses in the fetal alcohol syndrome: A report on twenty patients," J. Pediatr., 92:363–367 [1978]) was given to each mother at the time of delivery. Upon birth, infant meconium was collected and stored frozen at −70° C. until analysis.

Once the meconium samples were analyzed as described in Example 4, and the responses to the questionnaire reviewed, the results were then statistically analyzed by the two-tailed, two sample t-test. The GC results indicated that ethyl linoleate was the predominant FAEE present in the samples that contained FAEE.

It was observed that the presence of ethyl linoleate in meconium was strongly associated with maternal self-report of the number of drinks per drinking session in the month prior to pregnancy (MP)(p<0.01), the first trimester (p <0.02), the second trimester (p<0.04), and the third trimester (p<0.02), as well as the number of drinks on the occasions when more alcohol than usual was consumed (p<0.04), the number of drinks required in order to feel the effects of alcohol (p<0.02), the number of drinks per drinking session averaged over the MP, first, second, and third trimesters (p<0.05), the average number of drinks per week throughout the MP and pregnancy (p<0.02), and the average number of drinking days per week throughout the MP and pregnancy (p<0.03).

However, the presence of ethyl linoleate in the meconium samples was not correlated to cigarette or marijuana use, except when both the number of joints smoked per occasion (p<0.01) and the number of days per week of marijuana use in the third trimester (p<0.04) was considered. The presence of ethyl linoleate in the meconium samples was also not correlated to cocaine use, except for the number of days per week of cocaine use in the third trimester (p<0.05). These results indicate that the presence of ethyl linoleate in meconium is associated with, and is relatively specific for maternal ethanol consumption.

These results clearly show that the present invention provides methods that are useful for the screening of neonates and infants for prenatal alcohol exposure. The present invention also provides means by which infants and neonates may be screened for prenatal alcohol exposure in situations in which the mothers may not be available, or if only maternal self-reporting of ethanol use is considered.

I claim:

1. A method of detecting at least one fatty acid ester in a sample suspected of containing a fatty acid ester, comprising the steps of:
    a) providing:
        i) a meconium sample,
        ii) at least one solvent, and
        iii) a column comprising a non-amine packing;
    b) contacting said meconium sample with said at least one solvent under conditions such that an extracted sample is produced;
    c) applying said extracted sample to said column;
    d) eluting at least one fatty acid ester from said column, to provide at least one eluted fatty acid ester; and
    e) detecting said at least one eluted fatty acid ester.

2. The method of claim 1, wherein said at least one solvent is selected from the group consisting of acetone and hexane.

3. The method of claim 1, wherein step d) further comprises eluting said at least one fatty acid ester from said column with hexane:ethyl acetate.

4. The method of claim 1, wherein said meconium sample is from a neonate suspected of suffering from prenatal exposure to alcohol.

5. The method of claim 1, wherein said meconium sample is from a neonate suspected of suffering from fetal alcohol syndrome.

6. The method of claim 5, wherein the mother of said neonate is suspected of being alcohol tolerant.

7. The method of claim 1, wherein said at least one fatty acid ester is produced from at least one teratogen, and wherein said teratogen is selected from the group consisting of ethanol, methanol, propanol, 1-propanol, 2-propanol, butanol, pentanol, octanol, bromoethanol, chloroethanol, dichloroethanol, and trichloroethanol.

8. The method of claim 7, wherein said teratogen is ethanol.

9. The method of claim 1, further comprising the step of analyzing said at least one eluted fatty acid ester by gas chromatography.

10. The method of claim 1, further comprising the step of analyzing said at least one eluted fatty acid ester by gas chromatography-mass spectroscopy.

11. The method of claim 1, wherein said column comprising a non-amine packing is selected from the group consisting of silica gel columns and C18 columns.

12. A method of detecting at least one fatty acid ethyl ester in a sample, comprising the steps of:
    a) providing:
        i) a meconium sample,
        ii) a water-miscible solvent,
        iii) a water-immiscible solvent, and
        iv) a column comprising a non-amine packing;
    b) contacting said meconium sample with said water-miscible solvent to provide a mixture;
    c) contacting said mixture with said water-immiscible solvent under conditions such that an extracted sample is produced;
    d) applying said extracted sample to said column;
    e) eluting at least one fatty acid ethyl ester from said column; and
    f) detecting said at least one eluted fatty acid ethyl ester.

13. The method of claim 12, wherein said water-miscible solvent comprises acetone.

14. The method of claim 12, wherein said water-immiscible solvent comprises hexane.

15. The method of claim 12, wherein said water-miscible solvent comprises acetone and said water-immiscible solvent comprises hexane.

16. The method of claim 12, wherein step e) further comprises eluting said at least one fatty acid ethyl ester from said column with hexane:ethyl acetate.

17. The method of claim 12, wherein said meconium sample is from a neonate suspected of suffering from prenatal exposure to alcohol.

18. The method of claim 12, wherein said meconium sample is from a neonate suspected of suffering from fetal alcohol syndrome.

19. The method of claim 18, wherein the mother of said neonate is suspected of alcohol tolerance.

20. The method of claim 1, further comprising the step of analyzing said at least one eluted fatty acid ethyl ester by gas chromatography.

21. The method of claim 1, further comprising the step of analyzing said at least one eluted fatty acid ethyl ester by gas chromatography-mass spectroscopy.

22. The method of claim 1, wherein said column comprising a non-amine packing is selected from the group consisting of silica gel columns and C18 columns.

23. A method of detecting at least one fatty acid ethyl ester from a sample comprising the steps of:
  a) providing:
    i) a meconium sample;
    ii) acetone;
    iii) hexane;
    iv) a silica gel column;
    v) hexane:ethyl acetate; and
    vi) a gas chromatography column;
  b) contacting said sample with said acetone and hexane, under conditions such that an extracted sample is produced;
  c) applying said extracted sample to said silica gel column;
  d) eluting said fatty acid ethyl esters from said column with said hexane:ethyl acetate; and
  e) analyzing said fatty acid ethyl esters by gas chromatography.

24. The method of claim 23, wherein said sample is from a neonate suspected of suffering from prenatal exposure to alcohol.

25. The method of claim 23, wherein said neonate's mother is tolerant to ethanol.

26. The method of claim 23, further comprising the step of analyzing said fatty acid ethyl ester by gas chromatography-mass spectroscopy.

* * * * *